United States Patent
Li (10) Patent No.: US 8,934,687 B2
(45) Date of Patent: Jan. 13, 2015

(54) IMAGE PROCESSING DEVICE, METHOD AND PROGRAM INCLUDING PROCESSING OF TOMOGRAPHIC IMAGES

(75) Inventor: Yuanzhong Li, Kanagawa-ken (JP)

(73) Assignee: Fujifilm Corporation, Tokyo (JP)

(*) Notice: Subject to any disclaimer, the term of this patent is extended or adjusted under 35 U.S.C. 154(b) by 329 days.

(21) Appl. No.: 13/480,346

(22) Filed: May 24, 2012

(65) Prior Publication Data
US 2012/0300997 A1    Nov. 29, 2012

(30) Foreign Application Priority Data

May 26, 2011  (JP) ................................ 2011/117821

(51) Int. Cl.
*G06K 9/00* (2006.01)
*G06F 19/00* (2011.01)

(52) U.S. Cl.
CPC .................................. *G06F 19/321* (2013.01)
USPC .......................................................... 382/128

(58) Field of Classification Search
None
See application file for complete search history.

(56) References Cited

U.S. PATENT DOCUMENTS

| | | | |
|---|---|---|---|
| 8,077,946 B2* | 12/2011 | Oosawa | 382/128 |
| 8,672,836 B2* | 3/2014 | Higgins et al. | 600/117 |
| 2003/0063785 A1* | 4/2003 | Oosawa | 382/128 |
| 2008/0016120 A1* | 1/2008 | Markovich et al. | 707/104.1 |
| 2008/0207997 A1* | 8/2008 | Higgins et al. | 600/114 |
| 2008/0267481 A1* | 10/2008 | Nakamura | 382/131 |
| 2009/0292175 A1* | 11/2009 | Akimoto et al. | 600/156 |
| 2010/0303330 A1* | 12/2010 | Moriya | 382/132 |
| 2011/0002515 A1 | 1/2011 | Futami et al. | |
| 2011/0004595 A1 | 1/2011 | Yamagishi et al. | |
| 2012/0300997 A1* | 11/2012 | Li | 382/128 |

FOREIGN PATENT DOCUMENTS

| | | |
|---|---|---|
| JP | 2002-253539 | 9/2002 |
| JP | 2008-259622 A | 10/2008 |
| JP | 2010-273854 A | 12/2010 |
| JP | 2011-10889 A | 1/2011 |
| JP | 2011-28730 A | 2/2011 |

OTHER PUBLICATIONS

K. Nakamura et al., "A machine learning approach for body part recognition based on CT images", Proceedings of the SPIE, vol. 6914, p. 69141U, 2008.
Notice of Grounds for Rejection dated Apr. 16, 2013, with English translation.
Notice of Grounds for Rejection dated Aug. 27, 2013, with English translation.

* cited by examiner

*Primary Examiner* — Tahmina Ansari
(74) *Attorney, Agent, or Firm* — McGinn IP Law Group, PLLC (57) ABSTRACT

Examination information of a subject is selected, and a body part of the subject, which is a body part of interest in the examination information, is obtained from the selected examination information. Then, the presence or absence of further examination information relating to the obtained body part is determined, and a display device is caused to display an indication of the presence or absence of further examination information together with the selected examination information.

20 Claims, 3 Drawing Sheets

IMAGE PROCESSING DEVICE, METHOD AND PROGRAM INCLUDING PROCESSING OF TOMOGRAPHIC IMAGES

BACKGROUND OF THE INVENTION

1. Field of the Invention

The present invention relates to an image processing device and an image processing method for processing a three-dimensional image formed by a plurality of tomographic images obtained by tomographic imaging of a subject, as well as a program for causing a computer to carry out the image processing method.

2. Description of the Related Art

In recent years, in the field of medical images, imaging diagnosis using a three-dimensional image of a subject taken with a modality, such as an X-ray CT (Computed Tomography) apparatus or MRI (Magnetic Resonance Imaging) apparatus, has begun to be conducted. In this case, doctors request a pathological examination department or an endoscopic examination department to conduct an examination, such as pathological examination or endoscopic examination, as necessary, and conduct definitive diagnosis based on the three-dimensional image and the result of examination, such as pathological examination or endoscopic examination. Further, a person in charge of the examination, such as pathological examination or endoscopic examination, may generate and check examination information of a patient with referencing the three-dimensional image of the same patient.

However, in general, the three-dimensional images are managed separately from the examination results obtained by the pathological examination department or the endoscopic examination department. Therefore, in order to conduct the definitive diagnosis, the doctors have to search and obtain the presence or absence of pathological examination information or endoscopic examination information of the patient and the result of each examination, respectively, and the person in charge of the examination, such as pathological examination or endoscopic examination, has to search and obtain the three-dimensional image of the patient. Therefore, there is a demand for a technique for reducing time and labor needed to obtain such related examination information.

U.S. Patent Application Publication No. 20100303330 (hereinafter, "Patent Document 1") has proposed an approach wherein a position of a pathological examination is associated and stored with a radiographic image (human body image), such as a CT or MRI image, in advance, and when the human body image is displayed on a monitor device, a marker indicating the position of the pathological examination, which has been stored with being associated with the human body image, is displayed at a corresponding position on the radiographic image displayed on the monitor device, and information (such as a pathological image or a pathological report) about the pathological examination of a tissue collected from the position of the pathological examination is displayed simultaneously with the human body image.

However, the method proposed in Patent Document 1 requires an operation to associate and store the position of the pathological examination with the radiographic image. Therefore, there is a demand for a more simple approach to checking the presence or absence of the pathological examination corresponding to the radiographic image without requiring this process.

SUMMARY OF THE INVENTION

In view of the above-described circumstances, the present invention is directed to reducing a burden imposed on the user when the user checks the presence or absence of related examination information, such as a three-dimensional image of a subject, before displaying and referencing the related examination information.

An aspect of the image processing device according to the invention includes: selecting means for selecting examination information of a subject; body part obtaining means for obtaining a body part of the subject, which is a body part of interest in the examination information, from the selected examination information; related information determining means for determining presence or absence of further examination information relating to the obtained body part; and display control means for causing a display device to display an indication of the presence or absence of further examination information together with the selected examination information.

An aspect of the image processing method according to the invention includes: selecting examination information of a subject; obtaining a body part of the subject, which is a body part of interest in the examination information, from the selected examination information; determining presence or absence of further examination information relating to the obtained body part; and causing a display device to display an indication of the presence or absence of further examination information together with the selected examination information.

An aspect of the image processing program according to the invention is an image processing program for causing a computer to function as: selecting means for selecting examination information of a subject; body part obtaining means for obtaining a body part of the subject, which is a body part of interest in the examination information, from the selected examination information; related information determining means for determining presence or absence of further examination information relating to the obtained body part; and display control means for causing a display device to display an indication of the presence or absence of further examination information together with the selected examination information.

A specific example of the "subject" herein is a human body; however, the subject may be an animal body, or the like.

The "examination information" herein refers to information for identifying an image showing a cross section of a three-dimensional image of the subject taken with a CT or MRI apparatus, pathological examination information or endoscopic examination information. The pathological examination information may include any information relating to pathological examination, and typical examples thereof include a pathological examination image and a pathological examination report. The endoscopic examination information may include any information relating to endoscopic examination, and typical examples thereof include an endoscopic examination image and an endoscopic examination report.

The "body part" herein does not refer to an organ, such as heart, liver, or the like, and refers to head, neck, chest, abdomen, pelvis, legs, or the like, which varies depending on the externally viewed position on the subject, or combined body parts including at least two adjacent body parts among these body parts. Examples of the combined body parts including adjacent two body parts are head-neck, chest-abdomen, and the like.

If there is the further examination information, the display controlling means may display on the display device an indicator for allowing display of the further examination information.

In the image processing device according to the invention, if the examination information is information relating to two or more body parts, such as an endoscopic image or a CT image, the body part obtaining means may obtain a body part, among the two or more body parts, relating to the examination information displayed on the display device, i.e., a part of the endoscopic image or CT image, and the display control means may change the displayed indication of the presence or absence of the further examination information relating to the selected body part according to the selected body part.

In the invention, the examination information may be an image showing a cross section of a three-dimensional image of the subject, and the further examination information may be the pathological examination information or the endoscopic examination information.

In this case, the body part obtaining means may obtain the body part by performing body part recognition on the selected image. Further, in this case, the related information determining means may determine the presence or absence of the pathological examination information or the endoscopic examination information of the subject based on the pathological examination report included in the pathological examination information or the endoscopic examination report included in the endoscopic examination information.

In the invention, the examination information may be the pathological examination information or the endoscopic examination information of the subject, and the further examination information may be an image showing a cross section of a three-dimensional image of the subject.

In this case, the body part obtaining means may obtain the body part based on the pathological examination report included in the selected pathological examination information or the endoscopic examination report included in the selected endoscopic examination information.

According to the present invention, examination information of a subject is selected, and a body part of the subject, which is a body part of interest in the examination information, is obtained from the selected examination information. Then, the presence or absence of further examination information relating to the obtained body part is determined, and a display device is caused to display an indication of the presence or absence of further examination information together with the selected examination information. Therefore, the user need not search for the further examination information from the server of each department to display the further examination information, as in conventional methods. Further, there is no need to specify a position on the axial image CI and associate the specified position with the position of the pathological examination, as in the technique taught in Patent Document 1. Thus, the burden imposed on the user when the user checks the presence or absence of further examination information relating to the body part of interest in the selected examination information is reduced.

DESCRIPTION OF THE PREFERRED EMBODIMENTS

Figure 1:
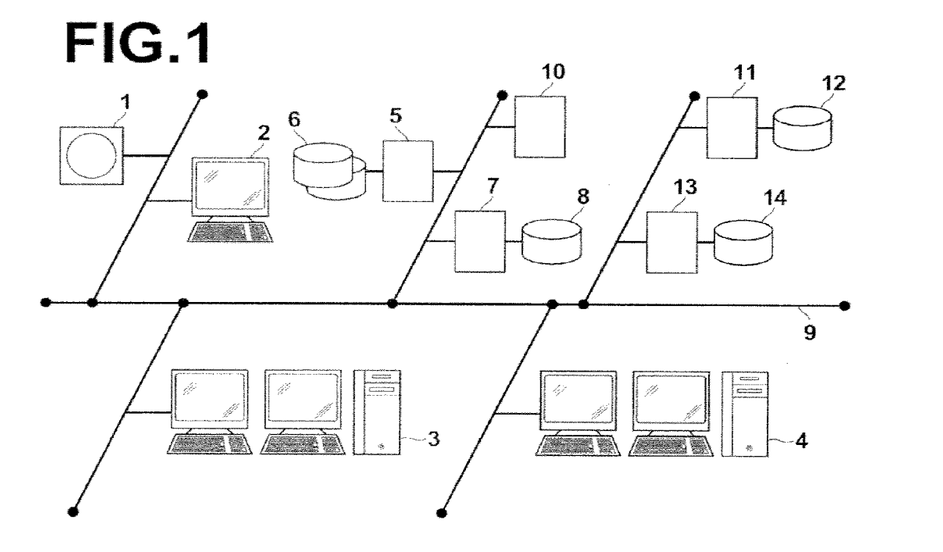
FIG. 1 is a diagram illustrating the schematic configuration of a medical information system, to which an image processing device according to embodiments of the present invention is applied.

Hereinafter, embodiments of the present invention will be described with reference to the drawings. In this description, identical components are denoted by the same reference numerals and explanation thereof may not be repeated. FIG. 1 is a diagram illustrating the schematic configuration of a medical information system incorporating an image processing device according to embodiments of the invention. This system is used for imaging a body part to be examined of a subject and storing the image based on an order of examination from a doctor of a diagnosis and treatment department, which is made using a known ordering system, conducting image interpretation of the taken image and generating an image interpretation report by a radiologist of a radiology department, and viewing the image interpretation report and conducting detailed observation of the image, which has been subjected to the image interpretation, by the doctor of the diagnosis and treatment department, who has requested the examination. As shown in FIG. 1, a medical imaging apparatus (modality) 1, an image quality check workstation (QA-WS) 2, a radiology department workstation 3, a diagnosis and treatment department workstation 4, an image information management server 5, an image information database 6, an image interpretation report server 7, an image interpretation report database 8, a pathological examination information management server 11, a pathological examination information database 12, an endoscopic examination information management server 13, an endoscopic examination information database 14 and an information management server 10 are connected to be able to communicate with each other via a network 9. These devices are controlled by a program installed from a recording medium, such as a CD-ROM. Alternatively, the program may be downloaded from a server connected via a network, such as the Internet, to be installed.

The modality 1 includes a device that images a body part to be examined of a subject to generate image data of an image showing the body part, and adds the image data with accompanying information defined by DICOM standard to output the image data with the accompanying information as image information. Specific examples of the modality include a CT apparatus, a MR apparatus, a PET apparatus, an ultrasound imaging apparatus, an X-ray imaging apparatus using a flat panel X-ray detector (FPD), etc. It should be noted that, in the following description, a set of the image data of the subject and the accompanying information thereof is referred to as the "image information". That is, the "image information" also includes text information relating to the image.

The QA-WS 2 is formed by a general-purpose processing unit (computer), one or two high-definition displays and an input device, such as a keyboard and a mouse. The processing unit has software installed therein for assisting operations by a medical technologist. Through functions implemented by execution of the software program, the QA-WS 2 receives the image information compliant to DICOM from the modality 1, and displays contents of the image data and the accompanying information contained in the received image information on a screen to prompt the medical technologist to check them. Thereafter, the QA-WS 2 transfers the image information checked by the medical technologist to the image information management server 5 via the network 9, and requests registration of the image information in the image information database 6.

The radiology department workstation 3 is a computer that is used by a radiologist of the radiology department to conduct image interpretation and generate an image interpretation report. The radiology department workstation 3 has a known hardware configuration including a CPU, a main storage device, an auxiliary storage device, an input/output interface, a communication interface, an input device, a display device, a data bus, etc., and has a known operation system, etc., installed therein. The radiology department workstation 3 includes a display device and one or two high definition displays. In this apparatus, operations, such as sending a request to view an image to the image information management server 5, displaying the image received from the image information management server 5, automatically detecting and highlighting an area in the image that is likely to be a lesion, assisting generation of an image interpretation report, sending a request to register or a request to view the image interpretation report to the image interpretation report server 7, displaying the image interpretation report received from the image interpretation report server 7, sending a request to register or a request to view patient information, etc., to the information management server 10, and displaying the patient information, etc., received from the information management server 10, are carried out by executing a software program for each operation.

The diagnosis and treatment department workstation 4 is a computer that is used by a doctor of the diagnosis and treatment department for detailed observation of an image, viewing an image interpretation report, viewing or inputting an electronic medical record, etc. The diagnosis and treatment department workstation 4 has a known hardware configuration including a CPU, a main storage device, an auxiliary storage device, an input/output interface, a communication interface, an input device, a display device, a data bus, etc., and has a known operation system, etc., installed therein. The diagnosis and treatment department workstation 4 includes a display device and one or two high definition displays. In this apparatus, operations, such as sending a request to view an image to the image information management server 5, displaying the image received from the image information management server 5, automatically detecting and highlighting an area in the image that is likely to be a lesion, sending a request to view an image interpretation report to the image interpretation report server 7, displaying the image interpretation report received from the image interpretation report server 7, sending a request to register or a request to view patient information, etc., to the information management server 10, and displaying the patient information, etc., received from the information management server 10, are carried out by executing a software program for each operation. The image processing device of the invention is implemented on this diagnosis and treatment department workstation 4. The diagnosis and treatment department workstation 4 has installed therein a software program for assisting diagnosis, as described herein, and the image processing disclosed herein is carried out by executing this software program, as will be described later.

The image information management server 5 is formed by a general-purpose computer with relatively high processing capacity, on which a software program for providing the function of a database management system (DBMS) is installed. The image information management server 5 is a so-called PACS (Picture Archiving and Communication Systems) server. The image information management server 5 includes a mass storage forming the image information database 6. This storage may be a large-capacity hard disk device connected to the image information management server 5 via a data bus or a disk device connected to a NAS (Network Attached Storage) or SAN (Storage Area Network) which is connected to the network 9.

In the image information database 6, the image data representing the subject image and the accompanying information are registered. The accompanying information may include, for example, an image ID for identifying each image, a patient ID for identifying the subject, an examination ID for identifying the examination session, a unique ID (UID) allocated for each image information, examination date and time when the image information was generated, the type of the modality used in the examination for obtaining the image information, the patient information, such as the name, the age and the sex of the patient, the examined body part (imaged body part), imaging conditions (whether or not a contrast agent was used, radiation dose, etc.), and a serial number or collection number of the image in a case where a plurality of images were taken in a single examination session. The image information may be managed in the form of XML or SGML data, for example.

When the image information management server 5 has received a request for registering the image information from the QA-WS 2, the image information management server 5 converts the image information into a database format and registers the information in the image information database 6.

Further, when the image management server 5 has received a request to view from the radiology department workstation 3 or the diagnosis and treatment department workstation 4 via the network 9, the image management server 5 searches the records of image information registered in the image information database 6 and sends the image information extracted through the search to the radiology department workstation 3 or the diagnosis and treatment department workstation 4 which has sent the request.

As the user, such as the radiologist or the doctor of the diagnosis and treatment department, has made an operation to request to view an image of interest for interpreting or observing the image, the radiology department workstation 3 or the diagnosis and treatment department workstation 4 sends the request to view to the image management server 5 and obtains the necessary image information. Then, the image information is displayed on the monitor screen and an operation, such as automatic detection of a lesion, is carried out in response to a request from the user. Further, the radiology department workstation 3 or the diagnosis and treatment department workstation 4 sends a request to view the patient information, etc., by the user, such as the radiologist or the doctor of the diagnosis and treatment department, to the information management server 10 to obtain the necessary information and display the information on the screen.

The radiology department workstation 3 displays on the monitor a report generation screen for assisting generation of the image interpretation report. When a text representing the content of findings, etc., based on the image interpretation by the radiologist is inputted, the radiology department workstation 3 generates the image interpretation report which contains the inputted information and the image used for the image interpretation (hereinafter, "interpreted image"). In the case where there are more than one interpreted images, the image interpretation report contains a representative image that best represents the findings in the image interpretation (hereinafter, "representative image"). The radiology department workstation 3 transfers the generated image interpretation report to the image interpretation report server 7 via the network 9, and sends a request to register the image interpretation report to the image interpretation report database 8.

The image interpretation report server 7 is formed by a general-purpose computer with relatively high processing capacity, on which a software program for providing the function of a database management system (DBMS) is installed. When the image interpretation report server 7 has received a request to register the image interpretation report from the radiology department workstation 3, the image interpretation report server 7 converts the image interpretation report into a database format and registers the image interpretation report in the image interpretation report database 8.

In the image interpretation report database 8, pieces of information, such as an image ID for identifying the interpreted image or representative image, a radiologist ID for identifying the radiologist who conducted image interpretation, positional information of an area of interest, findings and a confidence factor of the findings are registered. Besides them, an examination number and a patient number, which are obtained by referencing the accompanying information of the image information during image interpretation, as well as image data of the interpreted image or representative image may be included. The image data of the interpreted image or representative image may be reduced (decimated) image data having a lower number of pixels than that of the image data registered in the image information database 6. In this embodiment, link information (the address, the folder name, the file name, or the like, of the image data registered in the image information database 6) for allowing access to the original image data registered in the image information database 6 used to generate the reduced image data is also registered in the image interpretation report database 8. Alternatively, a copy of the image data registered in the image information database 6 may be registered in the image interpretation report database 8 without any conversion. Still alternatively, the positional information of the area of interest may be registered in the image information database 6 as a part of the accompanying information of the image data, rather than registered in the image interpretation report database 8. The image interpretation report may be managed in the form of XML or SGML data, for example.

When the image interpretation report server 7 has received a request to view from the radiology department workstation 3 or the diagnosis and treatment department workstation 4 via the network 9, the image interpretation report server 7 searches the records of image interpretation reports registered in the image interpretation report database 8, and sends the image interpretation report extracted through the search to the radiology department workstation 3 or the diagnosis and treatment department workstation 4 which has sent the request.

The pathological examination information management server 11 is formed by a general-purpose computer with relatively high processing capacity, on which a software program for providing the function of a database management system (DBMS) is installed. The pathological examination information management server 11 includes a mass storage forming the pathological examination information database 12. This storage may be a large-capacity hard disk device connected to the pathological examination information management server 11 via a data bus or a disk device connected to a NAS (Network Attached Storage) or SAN (Storage Area Network) which is connected to the network 9. The pathological examination information management server also includes a communication interface for communication with the modality 1, the image interpretation workstation 2, etc., via the network 9. The pathological examination information database 12 stores pathological examination images and pathological examination reports. The pathological examination report includes the patient ID, information for identifying the pathological examination image, such as the file name of the pathological examination image, which is the object of the report, and the address of a location storing the file, information indicating an organ or position of interest in the pathological examination image, etc.

When the pathological examination information management server 11 has received a request to view from the image interpretation workstation 2 via the network 9, the pathological examination information management server 11 searches the records of pathological examination information registered in the pathological examination information database 12, and sends the information extracted through the search to the image interpretation workstation 2 which has sent the request.

The endoscopic examination information management server 13 is formed by a general-purpose computer with relatively high processing capacity, on which a software program for providing the function of a database management system (DBMS) is installed. The endoscopic examination information management server 13 includes a mass storage forming the endoscopic examination information database 14. This storage may be a large-capacity hard disk device connected to the endoscopic examination information management server 13 via a data bus or a disk device connected to a NAS (Network Attached Storage) or SAN (Storage Area Network) which is connected to the network 9. The endoscopic examination information management server 13 also includes a communication interface for communication with the modality 1, the image interpretation workstation 2, etc., via the network 9. The endoscopic examination information database 14 stores endoscopic examination images and endoscopic examination reports. The endoscopic examination report includes the patient ID, information for identifying the endoscopic examination image, such as the file name of the endoscopic examination image, which is the object of the report, and the address of a location storing the file, information indicating an organ or position of interest in the endoscopic examination image, etc. The endoscopic examination images stored in the endoscopic examination information database 14 include not only still images but also moving images.

When the endoscopic examination information management server 13 has received a request to view from the image interpretation workstation 2 via the network 9, the endoscopic examination information management server 13 searches the records of endoscopic examination information registered in the endoscopic examination information database 14, and sends the information extracted through the search to the image interpretation workstation 2 which has sent the request.

The network 9 is a local area network for connecting various apparatuses and devices in a hospital with each other. However, in the case where the radiology department workstation 3 or the diagnosis and treatment department workstation 4 is also located in another hospital or clinic, the network 9 may be the Internet or a dedicated line connecting the local area networks of the hospitals with each other. In either case, the network 9 may preferably be a network, such as an optical network, that is able to achieve high speed transfer of the image information.

The information management server 10 is a so-called RIS (Radiology Information System: radiology department information system) server. The information management server 10 performs information processing, such as transferring information (such as an examination order or a diagnosis order to request the radiology department to image a patient, which is sent using the terminal 3 or 4 located at the radiology department or another department, such as the internal department or the surgical department, via the network 9, and the state of imaging operation of the modality 1), and making a request to register or view the patient information. Further, the information management server 10 manages, for each patient, various information, such as the patient information, diagnosis and treatment information, the examination information, accounts information, etc. The patient information is information for identifying each patient, and may include, for example, patient name, patient ID, etc. The patient information may also include present address, date of birth, age, sex, family make-up and whether the patient has a previous history of a disease or an allergy.

The diagnosis and treatment information is information about diagnosis of the patient, and may include, for example, consultation date, name of the diagnosis and treatment department, name of disease, diagnostic result, duration of therapy, type and amount of administered medicine, name of pharmacy, etc. The duration of therapy refers to a period of time for which the patient attended a medical institution for treatment of a disease. In the embodiments disclosed herein, the diagnostic result includes the presence or absence of definitive diagnosis and the result of definitive diagnosis, and the diagnosis and treatment information includes the examination information. The examination information includes information of a medical image taken for diagnosis, etc., and may specifically include examination date, examination equipment, examination method, examined body part, etc. The examination method refers to orientation of the patient relative to the modality during imaging, whether or not a contrast agent was used, etc. The examined body part refers to a body part of interest in the examination, such as head, neck, chest, abdomen, pelvis, legs, or a combination of two or more of these body parts. The accounts information may include information about expenses for medical activities, such as consultation, administration of drug, examination, etc., and whether or not a medical insurance is applied, etc.

Figure 2:
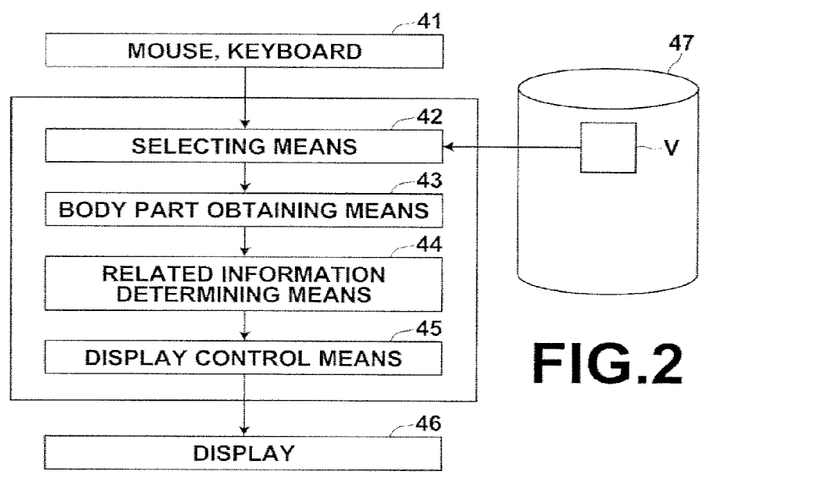
FIG. 2 is a functional block diagram of the image processing device of a first embodiment.

FIG. 2 is a block diagram schematically illustrating the configuration of a medical image displaying system, to which the medical image processing device implemented in the above-described medical information system according to a first embodiment of the invention is applied.

In this embodiment, the diagnosis and treatment department workstation 4 (image processing device) includes: an input means 41 (input device), such as a mouse and a keyboard; a storing means 47 formed by a storage device, such as a hard disk and a memory; a selecting means 42 for selecting the examination information of the subject; a body part obtaining means 43 for obtaining, from the selected examination information, the body part of the subject, which is the body part of interest in the examination information; a related information determining means 44 for determining the presence or absence of further examination information relating to the obtained body part; and a display control means 45 for causing the display device (display means) 46 to display an indication of the presence or absence of further examination information together with the selected examination information.

In this embodiment, a case where the examination information is an image showing a cross section of a three-dimensional image of the subject, and the further examination information is the pathological examination information or the endoscopic examination information is described as an example.

When the user has inputted an instruction specifying an image to be displayed to the diagnosis and treatment department workstation 4 prior to the image processing of the invention, the image information management server 5 reads out the registered three-dimensional image together with the accompanying information and information about the result of body part recognition from the image information database 6, and sends them to the diagnosis and treatment department workstation 4. In this manner, a three-dimensional image V of the chest and abdomen of the subject taken with the CT apparatus (modality 1) is loaded from the image information database 6 to the diagnosis and treatment department workstation 4, and the loaded three-dimensional image V is displayed on the display 46 for observation by the user, who is a doctor of the diagnosis and treatment department.

First, the display control means 45 displays axial images forming the three-dimensional image V one by one with changing the displayed image according to specification by the user made on the display screen via the input means 41, or the like. Then, the selecting means 42 selects the displayed axial image CI.

Then, the body part obtaining means 43 obtains the axial image CI selected by the selecting means 42, and recognizes and obtains the body part of the subject shown in the obtained axial image CI. The "body part" herein refers to at least one of head, neck, chest, abdomen, pelvis, legs, or combined body parts including at least two adjacent body parts among these body parts. In this embodiment, if the examination information relates to two or more body parts, such that the selected three-dimensional image V contains the chest and the abdomen, for example, the body part obtaining means 43 obtains the body part shown in the axial image CI displayed on the display device 46 among the two or more body parts.

Now, a body part obtaining operation performed by the body part obtaining means 43 is described. In this example, the method taught in K. Nakamura et al., "A machine learning approach for body part recognition based on CT images", Proceedings of the SPIE, Vol. 6914, p. 69141U, 2008, is used. In this manner, the body part recognized for each displayed tomographic image is obtained. For example, the body part is recognized and obtained as the chest through the body part recognition of the displayed axial image CI.

For the body part obtaining operation performed by the body part obtaining means 43, the technique taught in U.S. Patent Application Publication No. 20080267481 may be used, for example. This technique involves normalizing a plurality of inputted tomographic images, calculating a number of feature quantities from the normalized tomographic images, inputting the feature quantities calculated for each normalized tomographic image to classifiers, which are obtained through AdaBoosting, to calculate a body part score for each body part, which indicates likelihood of each tomographic image showing that body part, and determining the body part shown in each tomographic image by using the calculated body part scores as inputs and dynamic programming such that the order of body parts of a human body is maintained. Alternatively, a method using template matching of category (see, for example, Japanese Unexamined Patent Publication No. 2002-253539) or a method using eigenimages of each body part (see, for example, U.S. Patent Application Publication No. 20030063785) may be used.

The related information determining means 44 obtains the patient ID of the patient, who is the subject of the image CI selected by the selecting means 42, and obtains the body part shown in the displayed axial image CI. Then, based on the pathological examination report included in the pathological examination information or the endoscopic examination report included in the endoscopic examination information, the related information determining means 44 determines the presence or absence of the pathological examination information or the endoscopic examination information of the subject. Specifically, based on the patient ID, the related information determining means 44 searches through the pathological examination information database 12 and the endoscopic examination information database 14 to identify the pathological examination information and the endoscopic examination information corresponding to the patient ID and relating to the obtained body part.

In the case where the three-dimensional image V shows the chest and the abdomen, and the displayed axial image CI is an axial image at a certain position of the chest, the related information determining means 44 determines the presence or absence of the examination information for all the organs or examined elements contained in the chest. On the other hand, if the displayed axial image CI is an axial image at a certain position of the abdomen, the related information determining means 44 determines the presence or absence of the examination information for all the organs or examined elements contained in the abdomen.

It is assumed here that, prior to the image processing of this embodiment, an association table for associating each body part, such as chest, abdomen, etc., with key words relating to elements contained in the body part (key words relating to the body part to be examined), such names of an organ and components forming the organ contained in the body part, is stored in the storing means 47. The related information determining means 44 references the association table to obtain the key words relating to the examined body part associated with the obtained body part, identifies the pathological examination report or the endoscopic examination report of the subject containing the key words relating to the examined body part, and determines the presence or absence of the related information based on the presence or absence of the identified report. If there is the identified pathological examination report or endoscopic examination report, a pathological examination result image or an endoscopic image associated with or described in the report is further identified and the identified image is loaded from the pathological examination information database 12 and/or the endoscopic examination information database 14 to the storing means 47.

Figure 3:
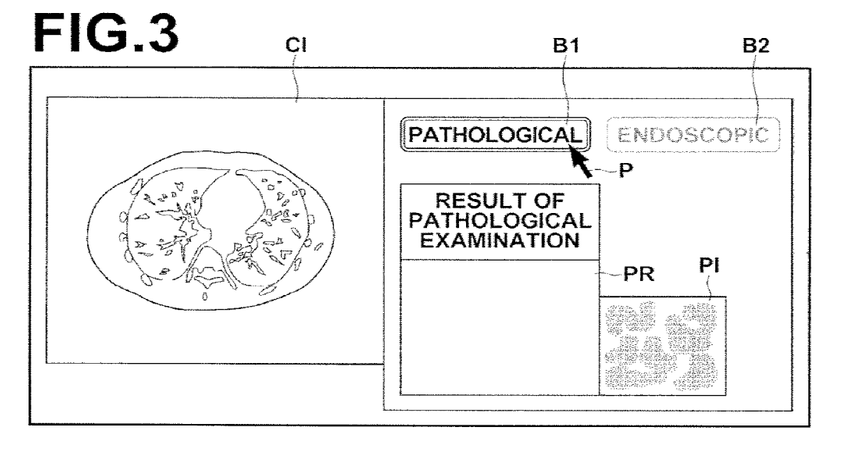
FIG. 3 is a diagram illustrating an example of a display screen displayed through image processing of the first embodiment.

Then, the display control means 45 displays, on the display 46, an indication of the presence or absence of the pathological examination information or the endoscopic examination information of the selected image CI and the body part shown in the image CI in a distinguishable manner according to the presence or absence of the related information obtained by the related information determining means 44. FIG. 3 is a diagram illustrating an example of the display screen displayed through the image processing according to the first embodiment. As shown in FIG. 3, in this embodiment, if there is the pathological examination information or the endoscopic examination information (the further examination information), the display control means 45 displays on the display device an indicator (a display button B1, B2), which allows display of the pathological examination information or the endoscopic examination information. In this example, as shown in FIG. 3, if there is the pathological examination information (the further examination information), the display button B1 is displayed in a selectable manner, and if there is no endoscopic examination information (further examination information), the display button B2, which is unselectable by the user, is distinguishably displayed in a lighter color.

Then, if there is a pathological examination image PI and/or a pathological examination report PR, as shown in FIG. 3, the display control means 45 detects an operation by the user moving a pointer P with a mouse, or the like, and clicking on the display button B1, and displays, as the pathological examination information, the pathological examination image PI and/or the pathological examination report PR determined by the related information determining means 44. Although FIG. 3 shows the case where there is no pathological examination information and there is the endoscopic examination information, if there is the endoscopic examination information, the display control means 45 detects clicking on the display button B2 by the user in the same manner and displays the endoscopic examination image and/or the endoscopic examination report as the endoscopic examination information.

In this embodiment, in the case where the selected three-dimensional image V relates to two or more body parts (the abdomen and the chest), when the user has changed the displayed axial image forming the three-dimensional image V, the display control means 45 changes the displayed indication of the presence or absence of the pathological examination information and the endoscopic examination information relating to the selected body part according to the body part (selected body part) shown in the image CI being displayed. For example, if the displayed axial image CI is an axial image of the chest, as shown in FIG. 3, only the presence or absence of the examination information, i.e., the pathological examination information and the endoscopic examination information, relating to the chest is indicated by the above-described display buttons B1, B2. On the other hand, if the displayed axial image CI is an axial image of the abdomen, only the presence or absence of the examination information, i.e., the pathological examination information and the endoscopic examination information, relating to the abdomen is indicated by the above-described display buttons B1, B2.

Alternatively, the display buttons B1, B2 in the above-described embodiment may be displayed only when there is the pathological examination information or the endoscopic examination information (further examination information), and may not be displayed when there is no pathological examination information or endoscopic examination information (further examination information).

As described above, in the first embodiment, the examination information of the subject is selected, the body part of the subject, which is the body part of interest in the examination information, is obtained from the selected examination information, the presence or absence of further examination information relating to the obtained body part is determined, and the display device is caused to display the indication of the determined presence or absence of further examination information together with the selected examination information. Therefore, the user need not search for the further examination information from the server of each department to display the further examination information, as in conventional methods. Further, there is no need to specify a position on the axial image CI and associate the specified position with the position of the pathological examination, as in the technique taught in Patent Document 1. Thus, the burden imposed on the user when the user checks the presence or absence of further examination information relating to the body part of interest in the selected examination information is reduced.

Further, in the first embodiment, there is no need to specify a position on the axial image CI and associate the specified position with the position of the pathological examination and display an indicator of the specified position on the axial image, as in the technique taught in Patent Document 1. Therefore, visual recognition of the axial image during diagnosis is facilitated. When the related information is associated based on the specified position, as taught in Patent Document 1, it is difficult to accurately associate the specified position in a soft organ having an unstable shape, such as the liver. Even when it is impossible to accurately understand the related examination information and the position, the effect of assisting diagnosis is sufficiently provided by presenting the indication of the presence or absence of related examination information or the related examination information itself. By extracting and displaying the related information according to the body part, such as neck, chest, abdomen, pelvis, legs or combined body parts including at least two adjacent body parts among these body parts, shown in the axial image, as in this embodiment, the user need not do the troublesome operation, and sufficient information necessary for diagnosis is extracted and presented to the user.

Still further, in this embodiment, if there is the further examination information, the display control means 45 displays on the display device the indicator which allows display of the further examination information. Therefore, the user can easily know the presence or absence of the further examination information. Since the further examination information is displayed as necessary, the invention is also preferably applicable to the user who does not want to always display the examination information. It should be noted that the invention is not limited to this embodiment, and the image processing device of the invention may use any technique that allows the user to know the presence or absence of further examination information, such as displaying the further examination information itself on the screen when there is the further examination information, for example.

Yet further, in the case where the examination information relates to two or more body parts, the body part obtaining means 43 obtains the body part relating to the examination information being displayed on the display device, and the display control means changes the indication of the presence or absence of further examination information relating to the selected body part according to the selected body part. Even when the three-dimensional image V relates to two or more body parts, it is highly possible that the displayed body part is the body part of interest for the user. Therefore, only the related information relating to the body part of interest can be synchronously displayed as important information for diagnosis without displaying too much unnecessary information, thereby facilitating the user to understand necessary information and improving the efficiency of diagnosis.

In the case where the examination information is an image showing a cross section of the three-dimensional image V of the subject and the further examination information is the pathological examination information or the endoscopic examination information, as in this embodiment, the pathological examination information or the endoscope information, which is important information for definitive diagnosis, can be presented as the related information based on the axial image, which is conventionally often referenced during diagnosis. Therefore, the image processing device of the invention is highly useful for diagnosis and improves the efficiency of diagnosis.

Further, in the above-described case, the related information determining means 44 determines the presence or absence of the pathological examination information or the endoscopic examination information of the subject based on the pathological examination report included in the pathological examination information or the endoscopic examination report included in the endoscopic examination information. Therefore, the presence or absence of the pathological examination information or the endoscopic examination information can be determined easily.

Figure 4:
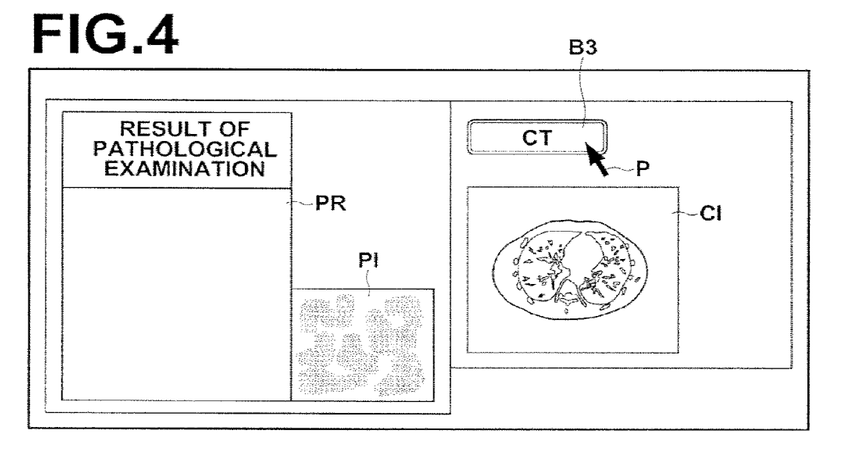
FIG. 4 is a diagram illustrating an example of a display screen displayed through image processing of a second embodiment.

Next, the image processing device 4 according to a second embodiment is described using FIG. 4. FIG. 4 is a diagram illustrating an example of a display screen displayed through image processing according to the second embodiment. In the second embodiment, a computer terminal (not shown in FIG. 1), which is used by a person in charge of pathological examination of the pathological examination department, has the function of the image processing device. The difference between the image processing device of the second embodiment and the image processing device of the first embodiment lies in that, in the second embodiment, the examination information is the pathological examination information and the further examination information is the three-dimensional image V taken with a CT or MRI apparatus. In the following description, different points from the first embodiment are mainly explained, and explanation of the common operations is omitted.

In the second embodiment, the selecting means 42 selects the pathological examination image PI or the pathological examination report PR being displayed according to specification by the user. Then, the body part obtaining means 43 obtains the body part of the subject described in the pathological examination report included in the selected pathological examination information. Specifically, using the association table similar to that in the first embodiment, key words registered in the association table are searched through the pathological examination report PR, and the body part associated with the searched out key words is obtained.

Then, the related information determining means 44 identifies the three-dimensional image(s) V of the subject in the image information database 6 based on the patient ID contained in the pathological examination report, and identifies the three-dimensional image V relating to the body part, which is obtained based on the pathological examination report, using header information of the three-dimensional image V. Alternatively, the related information determining means 44 may sample the axial images forming the three-dimensional image V at predetermined intervals or predetermined positions, and perform image recognition of the obtained axial images, as described in the first embodiment, to determine whether or not the three-dimensional image V shows the obtained body part.

Then, the display control means 45 displays the indication of the presence or absence of the three-dimensional image determined by the related information determining means 44. Similarly to the first embodiment, if there is the three-dimensional image V, the display control means 45 makes a button B3, which allows display of the CT image, selectable by the user to indicate that there is the related three-dimensional image V.

According to the second embodiment, the examination information is the pathological examination information and the further examination information is the three-dimensional image V taken with a CT or MRI apparatus. Therefore, a person in charge of pathological examination can easily reference the three-dimensional image V relating to the body part of interest in the pathological examination information without searching through the three-dimensional images V in the image information database 6, and therefore can easily and accurately understand the pathological examination information using the related further examination information.

Figure 5:
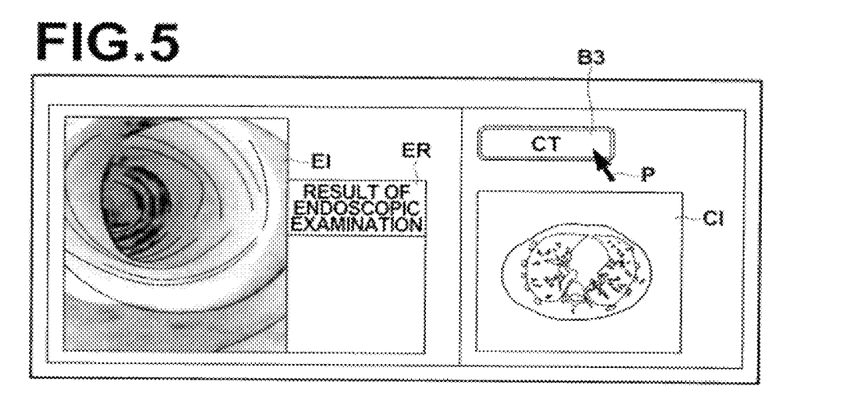
FIG. 5 is a diagram illustrating an example of a display screen displayed through image processing of a third embodiment.

Next, the image processing device according to a third embodiment is described using FIG. 5. FIG. 5 is a diagram illustrating an example of a display screen displayed through image processing according to the third embodiment. In the third embodiment, a computer terminal (not shown in FIG. 1), which is used by a person in charge of examination of the endoscopic examination department, has the function of the image processing device. The difference between the image processing device of the third embodiment and the image processing device of the first embodiment lies in that, in the third embodiment, the examination information is the endoscopic examination information, and the further examination information is the three-dimensional image V taken with a CT or MRI apparatus. In the following description, different points from the first embodiment are mainly explained, and explanation of the common operations is omitted.

In the third embodiment, the selecting means 42 selects an endoscopic examination image EI or an endoscopic examination report ER being displayed according to specification by the user. It is assumed in the third embodiment that, for each endoscopic examination image EI, an endoscopic examination report, which contains information identifying the endoscopic examination image EI, such as the name of the image file of the endoscopic examination image EI, and findings in the endoscopic examination, has been generated. Then, the body part obtaining means 43 obtains the body part of the subject described in the endoscopic examination report included in the selected endoscopic examination information. Specifically, using the association table similar to that in the first embodiment, key words registered in the association table are searched through the endoscopic examination report ER, and the body part associated with the searched out key words is obtained.

Then, the related information determining means 44 identifies the three-dimensional image(s) V of the subject in the image information database 6 based on the patient ID contained in the endoscopic examination report, and identifies the three-dimensional image V relating to the body part, which is obtained based on the endoscopic examination report, using the header information of the three-dimensional image V. Alternatively, the related information determining means 44 may sample the axial images forming the three-dimensional image V at predetermined intervals or predetermined positions, and perform image recognition of the obtained axial images, as described in the first embodiment, to determine whether or not the three-dimensional image V shows the obtained body part.

Then, the display control means 45 displays the indication of the indication of the presence or absence of the three-dimensional image determined by the related information determining means 44. Similarly to the first embodiment, if there is the three-dimensional image V, the display control means 45 makes a button B3, which allows display of the CT image, selectable by the user to indicate that there is the related three-dimensional image V. Further, the display control means 45 may indicate that there is the image interpretation report corresponding to the three-dimensional image V by making a button (not shown) which allows display of the image interpretation report selectable by the user, and may display the image interpretation report in response to selection of this button by the user.

According to the third embodiment, the examination information is the endoscopic examination information and the further examination information is the three-dimensional image V taken with a CT or MRI apparatus. Therefore, a person in charge of endoscopic examination can easily reference the three-dimensional image V relating to the body part of interest in the endoscopic examination information without searching through the three-dimensional images V in the image information database 6, and therefore can easily and accurately understand the endoscopic examination information using the related further examination information.

Further, in the third embodiment, in the case where the endoscopic examination information relates to two or more body parts, such as an endoscopic image taken with an upper endoscope and including the esophagus, the stomach and the duodenum, it is preferred that the body part obtaining means 43 of the third embodiment automatically recognizes the displayed body part with a known method to obtain the displayed body part, the related information determining means 44 determines, based on the obtained body part and the patient ID, the presence or absence of the three-dimensional image V relating to the body part shown in the displayed image, and the display control means 45 displays the indication of the presence or absence of the three-dimensional image V relating to the body part shown in the displayed image. For example, if the displayed endoscopic image shows the esophagus, the presence or absence of the three-dimensional image V showing the neck including the esophagus may be displayed. If the displayed endoscopic image shows the stomach, the presence or absence of the three-dimensional image V showing the chest including the stomach may be displayed. In this case, similarly to the first embodiment, it is highly likely that the displayed image shows the body part of interest for the user. Therefore, by displaying only the presence or absence of the related information relating to the body part of interest for diagnosis depending on the displayed body part, effective aid for the user to understand the displayed body part is provided.

It should be noted that the body part obtaining means 43 of the third embodiment may use any known method for obtaining the body parts shown in the displayed endoscopic image. For example, a technique taught in U.S. Patent Application Publication No. 20090292175 is applicable. In this case, the body part obtaining means 43 may obtain the view point position of the endoscopic image, identify the organs, such as esophagus, stomach and duodenum, shown in the displayed endoscopic image based on the obtained position, and identify the body parts, such as neck, chest, etc., to which the identified organs belong.

The above-described embodiments may be combined with each other. The individual means forming the image processing device 4 may have the functions of the two corresponding means among those in the first, second and third embodiments or may have all the functions of the corresponding means in the first, second and third embodiments.

It should be noted that the present invention is not limited to the above-described embodiments. For example, some or all of the components of the image processing device may be implemented by a single workstation or may be implemented by one or more workstations, servers and storage devices connected via a network. These devices are controlled by the program for assisting diagnosis disclosed herein, which is installed from a recording medium, such as a CD-ROM. The program may be downloaded from a storage device, such as a server, connected via a network, such as the Internet, before being installed.

The above-described embodiments are also applicable to other embodiments without changing the principles thereof.

What is claimed is:
1. An image processing device comprising:
a selecting unit for selecting examination information of a subject;
a body part obtaining unit for obtaining a body part of the subject, which comprises a body part of interest in the examination information, from the selected examination information;

a related information determining unit for determining presence or absence of further examination information relating to the obtained body part; and a display controlling unit for causing a display device to display an indication of the presence or absence of further examination information together with the selected examination information, wherein the examination information comprises an image showing a cross section of a three-dimensional image of the subject, wherein the further examination information comprises pathological examination information or endoscopic examination information, wherein the related information determining unit identifies a report having a key word relating to the body part of interest of the examination information among pathological examination reports included in the pathological examination information or endoscopic examination reports included in the endoscopic examination information by using the key word, and wherein the related information determining unit determines a presence or an absence of the pathological examination information or the endoscopic examination information relating to the body part of the subject based on the presence or the absence of the identified report.

2. The image processing device as claimed in claim 1, wherein the body part comprises one of head, neck, chest, abdomen, pelvis, legs and combined body parts including at least two adjacent body parts among head, neck, chest, abdomen, pelvis and legs.

3. The image processing device as claimed in claim 2, wherein, if there is the further examination information, the display controlling unit displays on the display device an indicator for allowing display of the further examination information.

4. The image processing device as claimed in claim 1, wherein, if the examination information relates to two or more body parts, the body part obtaining unit obtains a body part relating to the examination information displayed on the display device among the two or more body parts, and the display controlling unit changes the displayed indication of the presence or absence of the further examination information relating to the selected body part according to the selected body part.

5. The image processing device as claimed in claim 1, wherein the body part obtaining unit obtains the body part by performing body part recognition on the selected image.

6. An image processing device, comprising:
a selecting unit for selecting examination information of a subject;
a body part obtaining unit for obtaining a body part of the subject, which comprises a body part of interest in the examination information, from the selected examination information;
a related information determining unit for determining a presence or an absence of further examination information together with the selected examination information,
a display controlling unit for causing a display device to display an indication of the presence or the absence of the further examination information together with the selected examination information,
wherein the examination information comprises pathological examination information or endoscopic examination information of the subject,
wherein the further examination information comprises an image showing a cross section of a three-dimensional image of the subject, and wherein the body part obtaining unit identifies a key word relating to the body part of interest of the examination information included in a pathological examination report included in the selected pathological examination information or an endoscopic examination report included in the selected endoscopic examination information by using the key word and obtains the body part of the subject relating the identified key word.

7. An image processing method comprising:
selecting examination information of a subject;
obtaining a body part of the subject, which comprises a body part of interest in the examination information, from the selected examination information;
determining presence or absence of further examination information relating to the obtained body part; and
causing a display device to display an indication of the presence or absence of further examination information together with the selected examination information,
wherein the examination information comprises an image showing a cross section of a three-dimensional image of the subject,
wherein the further examination information comprises pathological examination information or endoscopic examination information,
wherein the determining further identifies a report having a key word relating to the body part of interest of the examination information among pathological examination reports included in the pathological examination information or endoscopic examination reports included in the endoscopic examination information by using the key word, and
wherein the determining further determines a presence or an absence of the pathological examination information or the endoscopic examination information relating to the body part of the subject based on the presence or the absence of the identified report.

8. A non-transitory storage medium containing an image processing program for causing a computer to function as:
a selecting unit for selecting examination information of a subject;
a body part obtaining unit for obtaining a body part of the subject, which is a body part of interest in the examination information, from the selected examination information;
a related information determining unit for determining presence or absence of further examination information relating to the obtained body part; and
a display controlling unit for causing a display device to display an indication of the presence or absence of further examination information together with the selected examination information,
wherein the examination information comprises an image showing a cross section of a three-dimensional image of the subject,
wherein the further examination information comprises pathological examination information or endoscopic examination information,
wherein the related information determining unit identifies a report having a key word relating to the body part of interest of the examination information among pathological examination resorts included in the pathological examination information or endoscopic examination reports included in the endoscopic examination information by using the key word, and
wherein the related information determining unit determines a presence or an absence of the pathological examination information or the endoscopic examination information relating to the body part of the subject based on the presence or the absence of the identified report.

9. An image processing method, comprising:
selecting examination information of a subject;
obtaining a body part of the subject, which comprises a body part of interest in the examination information, from the selected examination information;
determining a presence or an absence of further examination information together with the selected examination information,
displaying an indication of the presence or the absence of the further examination information together with the selected examination information,
wherein the examination information comprises pathological examination information or endoscopic examination information of the subject,
wherein the further examination information comprises an image showing a cross section of a three-dimensional image of the subject, and
wherein the obtaining further identifies a key word relating to the body part of interest of the examination information included in a pathological examination report included in the selected pathological examination information or an endoscopic examination report included in the selected endoscopic examination information by using the key word and obtains the body part of the subject relating the identified key word.

10. A non-transitory storage medium containing an image processing program for causing a computer to function as:
a selecting unit for selecting examination information of a subject;
a body part obtaining unit for obtaining a body part of the subject, which comprises a body part of interest in the examination information, from the selected examination information;
a related information determining unit for determining a presence or an absence of further examination information together with the selected examination information,
a display controlling unit for causing a display device to display an indication of the presence or the absence of the further examination information together with the selected examination information,
wherein the examination information comprises pathological examination information or endoscopic examination information of the subject,
wherein the further examination information comprises an image showing a cross section of a three-dimensional image of the subject, and
wherein the body part obtaining unit identifies a key word relating to the body part of interest of the examination information included in a pathological examination report included in the selected pathological examination information or an endoscopic examination report included in the selected endoscopic examination information by using the key word and obtains the body part of the subject relating the identified key word.

11. The image processing device as claimed in claim 1, wherein the related information determining unit identifies a report having key words relating to the body part of interest of the examination information among pathological examination reports included in the pathological examination information or endoscopic examination reports included in the endoscopic examination information by using the key words.

12. The image processing device as claimed in claim 6, wherein the related information determining unit identifies a report having key words relating to the body part of interest of the examination information among pathological examination reports included in the pathological examination information or endoscopic examination reports included in the endoscopic examination information by using the key words.

13. The image processing method as claimed in claim 7, wherein the determining further identifies a report having key words relating to the body part of interest of the examination information among pathological examination reports included in the pathological examination information or endoscopic examination reports included in the endoscopic examination information by using the key words.

14. The image processing program as claimed in claim 8, wherein the related information determining unit identifies a report having key words relating to the body part of interest of the examination information among pathological examination reports included in the pathological examination information or endoscopic examination reports included in the endoscopic examination information by using the key words.

15. The image processing method as claimed in claim 9, wherein the determining further identifies a report having key words relating to the body part of interest of the examination information among pathological examination reports included in the pathological examination information or endoscopic examination reports included in the endoscopic examination information by using the key words.

16. The image processing device as claimed in claim 1, wherein, if the examination information relates to two or more body parts, the displaying unit further displays the related information according to the body part including at least two adjacent body parts among the two or more body parts.

17. The image processing device as claimed in claim 6, wherein, if the examination information relates to two or more body parts, the displaying unit further displays the related information according to the body part including at least two adjacent body parts among the two or more body parts.

18. The image processing method as claimed in claim 7, wherein, if the examination information relates to two or more body parts, the displaying further displays the related information according to the body part including at least two adjacent body parts among the two or more body parts.

19. The image processing program as claimed in claim 8, wherein, if the examination information relates to two or more body parts, the display controlling unit further displays the related information according to the body part including at least two adjacent body parts among the two or more body parts.

20. The image processing method as claimed in claim 9, wherein, if the examination information relates to two or more body parts, the displaying further displays the related information according to the body part including at least two adjacent body parts among the two or more body parts.

* * * * *